United States Patent [19]

Wells

[11] Patent Number: 4,956,300

[45] Date of Patent: Sep. 11, 1990

[54] AID FOR DETERMINING THE PRESENCE OF OCCULT BLOOD, METHOD OF MAKING THE AID, AND METHOD OF USING THE AID

[75] Inventor: Henry J. Wells, Beaumont, Tex.

[73] Assignee: Helena Laboratories Corporation, Beamount, Tex.

[21] Appl. No.: 661,273

[22] Filed: Oct. 16, 1984

Related U.S. Application Data

[63] Continuation of Ser. No. 337,143, Jan. 5, 1982, abandoned.

[51] Int. Cl.$^5$ ............... G01N 21/78; G01N 33/72
[52] U.S. Cl. ............... 436/66; 422/56; 422/57; 422/61; 427/2; 435/128; 436/169; 436/904
[58] Field of Search ............... 436/66, 904, 164, 169; 422/56, 57, 55, 58, 61; 435/28; 427/2

[56] References Cited

U.S. PATENT DOCUMENTS

| | | |
|---|---|---|
| Re. 28,575 | 10/1975 | Bauer . |
| 2,223,520 | 12/1940 | Ioannu . |
| 2,290,436 | 7/1942 | Kamlet . |
| 2,387,244 | 10/1945 | Compton et al. . |
| 2,394,140 | 2/1946 | Biscow . |
| 2,418,392 | 4/1947 | Bender . |
| 2,567,445 | 9/1951 | Parker . |
| 2,754,289 | 7/1956 | Meyer . |
| 2,773,906 | 12/1956 | Emerson . |
| 2,799,660 | 7/1957 | Nicholls et al. . |
| 2,800,457 | 7/1957 | Green et al. . |
| 2,800,458 | 7/1957 | Green . |
| 2,823,984 | 2/1958 | Mavrodineau . |
| 2,838,377 | 6/1958 | Fonner ............... 422/56 X |
| 2,848,308 | 8/1958 | Free . |
| 2,886,445 | 5/1959 | Rosenthal et al. . |
| 2,893,844 | 7/1959 | Cook . |
| 2,905,594 | 9/1959 | Morris . |
| 2,930,695 | 3/1960 | Rosner et al. . |
| 2,953,454 | 9/1960 | Berman . |
| 2,986,453 | 5/1961 | Collias et al. . |
| 3,012,976 | 12/1961 | Adams, Jr. et al. ............... 422/56 X |
| 3,012,976 | 12/1961 | Adams, Jr. et al. . |
| 3,017,879 | 1/1962 | Sapit et al. . |
| 3,034,922 | 5/1962 | Böe et al. . |
| 3,042,496 | 7/1962 | Fancher et al. . |
| 3,043,782 | 7/1962 | Jensen . |
| 3,057,723 | 10/1962 | Jeffreys et al. . |
| 3,066,081 | 11/1962 | Rorem et al. . |
| 3,092,463 | 6/1963 | Adams, Jr. et al. . |
| 3,092,464 | 6/1963 | Adams, Jr. et al. . |
| 3,092,465 | 6/1963 | Adams, Jr. et al. . |
| 3,116,223 | 12/1963 | Rosner et al. . |
| 3,183,173 | 5/1965 | Oakes . |
| 3,232,710 | 2/1966 | Rieckmann et al. . |
| 3,252,762 | 5/1966 | Adams, Jr. et al. . |
| 3,290,117 | 12/1966 | Adams, Jr. et al. . |
| 3,293,683 | 12/1966 | Wyant . |
| 3,350,278 | 10/1967 | Gretton et al. . |
| 3,406,015 | 10/1968 | Foster ............... 23/230 B |
| 3,406,106 | 10/1968 | Foster et al. . |
| 3,411,887 | 11/1968 | Chi-Choon Ku . |
| 3,418,079 | 12/1968 | Rey et al. . |
| 3,438,737 | 4/1969 | Atkinson et al. . |
| 3,443,903 | 5/1969 | Haack et al. . |
| 3,447,536 | 6/1969 | Snyder . |
| 3,453,180 | 7/1969 | Fraser, Jr. et al. . |
| 3,466,145 | 9/1969 | Duyne . |
| 3,472,738 | 10/1969 | Foster . |
| 3,507,269 | 4/1970 | Berry . |
| 3,509,872 | 5/1970 | Truhan . |
| 3,511,608 | 5/1970 | Anderson . |
| 3,526,480 | 9/1970 | Findl et al. . |
| 3,552,925 | 1/1971 | Fetter . |
| 3,558,435 | 1/1971 | Rey et al. . |
| 3,598,704 | 8/1971 | Dablgvist . |
| 3,625,654 | 12/1971 | Duyne . |
| 3,627,697 | 12/1971 | Rey et al. . |
| 3,627,698 | 12/1971 | Rey et al. . |
| 3,630,847 | 12/1971 | Rey et al. . |
| 3,630,957 | 12/1971 | Rey et al. . |
| 3,654,179 | 4/1972 | Bauer . |
| 3,654,180 | 4/1972 | Bauer . |
| 3,668,076 | 6/1972 | Rey et al. . |
| 3,672,351 | 6/1972 | Ubersax et al. . |
| 3,699,005 | 10/1972 | Foster . |
| 3,712,853 | 1/1973 | Rey et al. . |
| 3,713,772 | 1/1973 | Tavel . |
| 3,811,840 | 5/1974 | Bauer et al. ............... 422/56 |
| 3,814,668 | 6/1974 | Blake et al. . |
| 3,847,553 | 11/1974 | Verbeck ............... 435/28 X |

(List continued on next page.)

FOREIGN PATENT DOCUMENTS

| | | |
|---|---|---|
| 093595 | 11/1983 | European Pat. Off. . |
| 0006359 | 2/1972 | Japan ............... 422/56 |
| 0047359 | 2/1972 | Japan . |
| 1018563 | 1/1966 | United Kingdom . |

OTHER PUBLICATIONS

Miller, MD, Colorectal Cancer: Are the Goals of Early Detection Achieved?, vol. 27(6), 338–343 (1977).

Sherlock, MD, et al., Modern Approaches to Early Identification of Large–Bowl Cancer, vol. 19(10), 959–964 (1974).

Chemical Abstracts, 66:8780e, 878 in (1967).

*Primary Examiner*—Robert J. Hill, Jr.
*Attorney, Agent, or Firm*—Spencer & Frank

[57] ABSTRACT

A guaiac reagent-based diagnostic aid for determining the presence of occult blood in an aqueous system contains a micron-sized silica gel into which a guaiac solution has been adsorbed. The guaiac-containing carrier is contacted with a dry, particulate, oxidizing agent, such as a monopersulfate compound, to form a single composition. This composition can be packaged in a water-pervious sandwich. Upon contact with water, the oxidizing agent is activated to produce hydrogen peroxide, which in the presence of occult blood will oxidize the adsorbed guaiac to a brilliant blue reaction product.

13 Claims, No Drawings

U.S. PATENT DOCUMENTS

| | | | |
|---|---|---|---|
| 3,853,468 | 12/1974 | Haymond. | |
| 3,853,471 | 12/1974 | Rittersdorf et al. | |
| 3,853,472 | 12/1974 | Rittersdorf et al. | |
| 3,854,885 | 12/1974 | Fromm et al. | |
| 3,912,457 | 10/1975 | Ogawa et al. | |
| 3,917,452 | 11/1975 | Rittersdorf et al. | |
| 3,964,871 | 6/1976 | Hochstrasser. | |
| 3,975,161 | 8/1976 | Svoboda et al. | 422/56 |
| 3,975,161 | 8/1976 | Svoboda et al. | |
| 3,975,162 | 8/1976 | Renn. | |
| 3,986,833 | 10/1976 | Mast et al. | |
| 3,996,006 | 12/1976 | Pagano. | |
| 4,005,984 | 2/1977 | Alsop et al. | |
| 4,017,261 | 4/1977 | Svoboda et al. | |
| 4,035,150 | 7/1977 | Jaffe. | |
| 4,046,514 | 9/1977 | Johnston et al. | |
| 4,061,468 | 12/1977 | Lange et al. | |
| 4,063,894 | 12/1977 | Ogawa et al. | |
| 4,071,318 | 1/1978 | Lam. | |
| 4,092,120 | 5/1978 | Suovaniemi et al. | |
| 4,148,611 | 4/1979 | Nand et al. | |
| 4,175,923 | 11/1979 | Friend | 422/56 X |
| 4,219,336 | 8/1980 | Guthlein et al. | 422/56 X |
| 4,220,713 | 9/1980 | Rittersdorf et al. | |
| 4,251,222 | 2/1981 | White. | |
| 4,251,223 | 2/1981 | White. | |
| 4,260,393 | 4/1981 | Gibson. | |
| 4,269,938 | 5/1981 | Frank | 422/56 X |
| 4,277,250 | 7/1981 | Melnick et al. | |
| 4,278,439 | 7/1981 | White. | |
| 4,278,439 | 7/1981 | White. | |
| 4,292,272 | 9/1981 | Kitajima et al. | |
| 4,303,409 | 12/1981 | Ogawa et al. | |
| 4,310,626 | 1/1982 | Burkhardt et al. | |
| 4,329,317 | 5/1982 | Detweiler. | |
| 4,333,734 | 6/1982 | Fleisher. | |
| 4,365,970 | 12/1982 | Laurence et al. | |
| 4,385,114 | 5/1983 | Gëthlein et al. | |
| 4,447,542 | 5/1984 | Gantzer. | |
| 4,486,536 | 12/1984 | Baker et al. | |
| 4,493,892 | 1/1985 | Fleisher. | |
| 4,511,533 | 4/1985 | Guadagno. | |
| 4,541,987 | 9/1985 | Guadagno. | |
| 4,556,640 | 12/1985 | Gantzer. | |
| 4,578,358 | 3/1986 | Oksman et al. | |
| 4,725,553 | 2/1988 | Guadagno. | |
| 4,742,002 | 5/1988 | Guadagno. | |

AID FOR DETERMINING THE PRESENCE OF OCCULT BLOOD, METHOD OF MAKING THE AID, AND METHOD OF USING THE AID

This is a continuation of application Ser. No. 337,143 filed Jan. 5, 1982, now abandoned.

BACKGROUND OF THE INVENTION

The present invention relates to a home diagnostic aid and method for determining the presence of hemoglobin in an aqueous medium, and more particularly, to a diagnostic aid and method for determining the presence of occult blood in fecal matter present in an aqueous medium, and most particularly, to a diagnostic aid and method for determining the presence of occult blood in fecal matter with an easily used and comprehended test procedure that employs a single diagnostic aid in only a single manipulative step and eliminates the necessity of handling the fecal matter prior to or during the test procedure and the handling of the test materials once the test is completed.

Over 100,000 persons in the United States are affected by cancer of the colon and rectum per year, occurring equally in both the male and female. When the number of colorectal cancers occurring each year is combined with the number of cancers occurring in other digestive organs, including the esophagus and stomach, such cancers of the digestive system account for more occurrences of cancer than any other single form of the disease. Contrary to many other forms of cancer, early diagnosis and treatment of digestive tract cancer does result in a cure rate of 80% to 90% of those persons affected by the disease. If, however, the disease is not detected until the later stages, the cure rate can drop drastically to 25% or less. Thus, early detection of the disease is critical to successful treatment of digestive tract cancer.

Most, but not all, cancers of the digestive tract bleed to a certain extent. This blood is deposited on and in fecal matter excreted from the digestive system. The presence of blood in fecal matter is not normally detected, however, until gross bleeding, that is, blood visible to the naked eye, occurs. Most advanced cancers cause gross bleeding.

It is known that digestive tract cancers in the early stages also tend to bleed, giving rise to occult (hidden) blood in the fecal matter. Test equipment and test procedures have been developed for use by physicians in testing for the presence of occult blood in fecal matter. One of the most successful tests is manufactured and sold by Smith Kline Diagnostics of Sunnyvale, California, under the trademark "Hemoccult". The package for the "Hemocult" test is disclosed in U.S. Pat. No. 3,996,006 issued to J. F. Pagano. Briefly, the Pagano test employs an absorbent white paper impregnated with a guaiac reagent and encased in a special test slide having openable flaps on both sides of the test slide. To use the Pagano test slide, one must obtain a sample of fecal matter, smear it onto the guaiac-impregnated paper by opening the panel on one side of the test slide, and thereafter close the panel. A panel on the opposite side of the test slide is then opened and a developing agent, which is a stabilized solution of hydrogen peroxide and denatured alcohol, is applied to the guaiac-impregnated paper. If occult blood is present in the fecal matter smeared on the opposite side of the paper, the product of the guaiac reaction will appear as a blue substance against the white paper background, providing a positive indication of the presence of blood in the fecal matter.

Although the Pagano test is excellent for use by physicians in their offices and by diagnostic laboratories, it is not the type of test that is readily adaptable for use by the ordinary person because of his adverse reaction to handling fecal matter and because of his lack of skill in interpreting the results. As stated above, the Pagano test requires that a specimen of fecal matter be obtained. Normally, a specimen is obtained by procuring a sample on the end of a spatula or a wooden depressor, which is then used to smear the specimen on the paper in the Pagano test slide. Once the sample is obtained and the test procedure completed, both the test slide and the spatula or depressor must be disposed of. Disposal of the used materials can and does present a physical problem to, if not an adverse psychological reaction from, the ordinary person. Thus, the ordinary person is not likely to use the Pagano test because of its unclean nature (at least apparently so to the ordinary person) and because of the disposal problems associated with the used test slide and spatula or depressor. Additionally, the ordinary person does not necessarily have the skill required to analyze, and thus form accurate conclusions from, the test results.

As an alternative, the ordinary person can initiate the Pagano test in his home and then forward the test slide to his physician or a laboratory for addition of the developing agent and analysis of the test. This procedure, however, requires cold storage of the test slide and specimen if there is a significant time lapse before the test can be completed. Certainly, the ordinary person does not wish to store a fecal specimen in his household refrigerator, normally the only cold storage available to him, until he can present the specimen to his physician or an appropriate laboratory. Thus, the general public is not likely to follow or comply with this alternative.

Another test for occult blood is suggested by D. E. Fonner in U.S. Pat. No. 2,838,377. The Fonner test, as disclosed, can be effected in a toilet bowl containing fecal matter. The basic test reagents employed by Fonner are otolidine and benzidine. These reagents in the presence of blood and other reactants produce a dye visible to the naked eye. Although the Fonner test appears to be a solution to the problem of finding a viable home test for occult blood, it has not met with success for two reasons. First, the above-listed reagents are in themselves known to cause cancer and thus are not suitable for general public distribution. Additionally, the Fonner reagents have a relatively high rate of providing false indications of the presence of occult blood.

Thus, to date, the use of the Pagano test, the Fonner test, and other similar tests has been limited primarily to physicians and diagnostic laboratories. Although this limitation might not at first glance present a significant problem, it does limit the early detection of digestive tract cancers, primarily because patients will not see a physician until other symptoms of digestive tract cancers, such as gross bleeding, manifest themselves. Thus, early detection of cancer of the digestive tract still does not occur with the great majority of patients who contract the disease.

Until the advent of the present invention, the most viable method for testing for occult blood in the home is that disclosed by W. G. Friend in U.S. Pat. No. 4,175,923, assigned to Hematec Corporation of Bellevue, Wash. The Friend test again uses the reliable and time-proven test reagent guaiac. In accordance with the preferred embodiment disclosed by Friend, guaiac is impregnated on an absorbent substrate such as an absorbent laboratory filter paper. A developing solution, comprising an alcohol and peroxide, is applied to the guaiac-containing absorbent substrate. The activated test substrate is then deposited in a toilet bowl, for example, containing feces. If occult blood is present, the guaiac is oxidized to a blue dye that is visible against the absorbent substrate.

While the Friend test overcomes some of the drawbacks of the Pagano test and the Fonner test, the Friend test still has its disadvantages. First, the alcohol-guaiac solution is highly flammable, presenting a potential hazard to a user in the bathroom, a common smoking area. Secondly, the addition of the solution to the test substrate in both the Pagano and Friend tests will almost always leave a brown or blue green ring on the substrate unless the solution is evenly distributed over the entire substrate. This ring can easily be misinterpreted by the inexperienced person as a positive test result. As a consequence, it is desirable to eliminate these problems.

SUMMARY OF THE INVENTION

The present invention achieves the desired result by providing a diagnostic aid employing the guaiac reaction that is used by performing the single manipulative step of merely depositing a single package in an aqueous medium to be tested for the presence of occult blood. Once the package is in the aqueous medium, it is observed for the characteristic blue dye reaction to determine whether occult blood is present in the aqueous medium. All of the necessary components for causing guaiac to react in an aqueous medium are present in a single novel package in a dry form that does not require the addition of a liquid developer by the user, as has been required by all prior tests employing guaiac since the guaiac reaction was discovered over one hundred years ago.

The diagnostic aid, in accordance with the present invention, comprises an adsorbent carrier in contact with an oxidizing agent. The adsorbent carrier has adsorbed thereon a solution of guaiac in a solvent therefor. The oxidizing agent, comprised essentially of a monopersulfate compound, is capable of oxidizing the guaiac to a blue dye in the presence of water and hemoglobin. The oxidizing agent, in the absence of water, however, is substantially nonreactive with the guaiac adsorbed onto the carrier. Preferably, the carrier and oxidizing agents are dry, particulate materials. Once the carrier and oxidizing agent are deposited in an aqueous medium, they are observed for the presence of blue dye to indicate whether hemoglobin is present in the medium.

A diagnostic aid prepared in accordance with the present invention is inexpensive, clean, nontoxic, noncarcinogenic, and is otherwise safe to handle. The aid has a long shelf life and is very simple to use. Since a positive reaction by the aid yields a bright blue dye that is highly visible against the background of the carrier and/or the oxidizing agent, comprised essentially of a monopersulfate compound, the test is easily interpreted with little likelihood of error.

DETAILED DESCRIPTION OF THE INVENTION

The diagnostic aid manufactured in accordance with the present invention places all of the components necessary to yield a positive guaiac reaction in the presence of hemoglobin (one that produces a blue dye) into a single package containing only dry ingredients. To use the diagnostic aid, the single package need only be deposited in an aqueous medium containing the material to be tested for the presence of occult blood, for example, a toilet bowl containing feces. It is presently preferred that the single package be composed of dry material comprising (a) an adsorbent carrier onto which a guaiac solution has been adsorbed (or impregnated) and (b) a dry oxidizing agent capable of producing the required oxidizing compound upon contact with the aqueous medium in which the test is to be conducted. The carrier and oxidizing agent can both be particulate in form and are preferably white so that the blue dye produced by the guaiac reaction in the presence of hemoglobin can be readily observed by the naked eye. As will be understood by reading further, the single package constituting the reactive test system can also take forms other than a particulate mass.

The primary purpose of the carrier is to receive and hold guaiac in a form in which it will be readily available to react in the presence of hemoglobin and a suitable oxidizing agent. Since guaiac alone will not readily react with an oxidizing agent and hemoglobin in an aqueous environment, the guaiac is first dissolved in a solvent therefor and in accordance with the present invention is adsorbed onto an appropriate adsorbent substrate or carrier.

A variety of adsorbent carriers can be employed to adsorb and retain the guaiac in the diagnostic aid. The principal requirement for the carrier is that it must be capable of adsorbing a solution of guaiac and, once the solution is adsorbed, remain in an essentially dry state. Further, a mixture of appropriate carriers may be used. Most preferably, the carrier is in particulate form so that a guaiac solution can easily be combined and homogeneously mixed throughout the carrier. Silica-based materials including silica and silica gel, as well as calcium phosphate perform particularly well as particulate adsorbent carriers. A presently preferred carrier is the micron-sized silica gel marketed under the trade name "Syloid" by the Davison Chemical Division of W. R. Grace & Company of Baltimore, Md.

Heretofore, it was thought that only water-miscible solvents could be employed to dissolve guaiac in order to effectively obtain a reproducible guaiac reaction with hemoglobin in an aqueous medium. However, both water-miscible and immiscible solvents can be employed with the guaiac solution is adsorbed onto a carrier and oxidized in the presence of hemoglobin in an aqueous medium. Further, appropriate, compatible solvents may be utilized as mixtures. The preferred solvents, however, are the water-miscible solvents such as alkanols and alkenols having from one to six carbon atoms, and particularly the lower aliphatic alcohols. The most preferred alcohols include methanol and particularly isopropyl alcohol. Among the water-immiscible solvents that have been found efficacious are chloroform and benzene.

One of the primary objectives of the present invention is to produce a dry diagnostic aid that is comprised in a single composition or package. Therefore, since the guaiac solvent adsorbed in the carrier is preferably dry and particulate, it is incumbent that the oxidizing agent employed in the system also be in dry form. The oxidizing agent is preferably of the type that will yield hydrogen peroxide in the presence of water. The hydroperoxide, of course, is the oxidant that promotes the reaction between guaiac and hemoglobin to produce the blue reaction product. The oxidizing agent must be capable of being combined with the guaiac-containing carrier to form a single composition or package that will readily react in an aqueous system in the presence of blood. Additionally, the oxidizing agent must be relatively inert with respect to the guaiac in the absence of water. Yet, the oxidizing agent must readily yield its hydrogen peroxide in the presence of water so that the guaiac reaction will take place in a relatively short time after the diagnostic aid has been inserted into the aqueous reaction medium.

The presently preferred oxidizing agent is potassium monopersulfate, a white, granular, free-flowing powder. This monopersulfate compound is commercially available as a triple salt comprised of two mols of potassium monopersulfate, one mol of potassium hydrogen sulfate, and one mol of potassium sulfate under the trade name "Oxone" from E.I. DuPont de Nemours & Company, Inc. of Wilmington, Del.

It has also been found that liquid oxidizing agents can be adsorbed onto a suitable carrier, for example, a silica gel such as the Syloid composition identified above. Additionally, some of the soluble peroxide compounds and relatives thereof can also be dissolved and then adsorbed onto a similar silica gel. For example, hydrogen peroxide can be adsorbed onto a silica gel such as Syloid. Additionally, the peroxide compounds such as cumene hydroperoxide and tertiary butyl hydroperoxide can be dissolved in isopropyl alcohol or adsorbed directly onto a silica gel carrier. Although these latter oxidizing agents are effective to produce a noticeable and accurate guaiac reaction, none functions as well as the monopersulfate compound identified above. After the liquid or dissolved oxidizing agent is absorbed onto a suitable carrier, that carrier is then contacted with a guaiac-containing carrier to form a single composition.

In practice, guaiac can be combined with a solvent such as isopropyl alcohol in an amount from one to five percent by weight guaiac based on the total solution. It is preferred that from one to about three percent by weight of guaiac be employed in the solvent. The most preferred composition constitutes three percent by weight guaiac in isopropanol. The guaiac solution is combined with a silica gel carrier by slowing adding it to the silica gel while stirring the silica gel. It is preferred that the guaiac solution be combined with a silica gel carrier such as Syloid in proportions of from 1 ml of solution to 6 grams of carrier to 15 ml of solution to 1 gram of carrier. It is most preferable, however, that on the order of one ml of solution per gram of carrier be employed so that the test is not overly sensitive.

When a particulate oxidizing agent such as a monopersulfate compound is employed, the guaiac-containing carrier is combined with an oxidizing agent in a weight range of from one part guaiac-containing carrier to three parts oxidizing agent, to three parts by weight guaiac-containing carrier to one part oxidizing agent. A one-to-one proportion is the most preferred at the present time as it yields the most vivid guaiac reaction in the presence of hemoglobin.

In order to yield an effective diagnostic aid, the guaiac-containing carrier as well as the oxidizing agent must be placed in intimate contact with each other and maintained in contact when placed in an aqueous environment to determine whether occult blood is present in that environment. A variety of packaging techniques may be employed to maintain contact between the guaiac-containing carrier and the oxidizing agent. For example, nonwoven liquid-pervious mats such as filter paper can be employed. The guaiac-containing carrier and oxidizing agent can be thoroughly intermixed and placed on or can be layered on a first liquid-pervious mat followed by an overlay of the second mat to form a water-pervious sandwich. The periphery of the sandwich can be adhesively secured to retain the carrier and oxidizing agent within the sandwich. When the sandwich is placed in a water environment, water plus any occult blood passes through the filter paper and comes into contact with the oxidizing composition and guaiac reagent. If occult blood is present, the oxidation reaction produces the characteristic blue reaction product. One particularly efficacious filter paper has been found to be one available from The Dexter Corporation, Windsor Locks, Conn. This material is very similar to that employed in a conventional tea bag.

As an alternative to the foregoing packaging technique, the oxidizing agent can be dissolved in a suitable solvent and impregnated into a suitable liquid-pervious substrate, such as the filter paper described above. The solvent can then be evaporated leaving the dry oxidizing agent in the substrate. For example, an oxidizing agent such as potassium monopersulfate can be dissolved in water. The resulting solution can then be absorbed by a filter paper substrate. Thereafter the filter paper can be air dried, evaporating the solvent and leaving the oxidizing agent in the paper. A guaiac-containing carrier can then be placed on the substrate followed by an overlay of a liquid-pervious mat to provide all of the required test reactants in a single package.

Another alternative contemplated by the present invention is that the oxidizing agent be dissolved in an appropriate solvent and adsorbed onto an absorbent carrier. The same carrier material may also have guaiac adsorbed thereon.

In addition to the foregoing packaging techniques, it is possible to adhesively secure the guaiac-containing carrier to one side, for example, of a liquid-pervious filter paper while the oxidizing agent is adhesively secured to the opposing side of the paper. Additionally, the materials can be compressed into tablet form with a suitable binder. It is also possible to include an effervescing material in tablet or layered form that will react upon contact with water to produce a gas, which in turn will tend to mix the contents of the aqueous medium and enhance the guaiac reaction if occult blood is present.

As will be readily recognized by one of ordinary skill, the present invention represents a significant advance over prior art diagnostic aids employing the guaiac reaction. All that need be done with the single composition system, which includes the guaiac-containing carrier and oxidizing agent, is to place the composition in an aqueous medium, such as a toilet bowl, the contents of which are to be tested for occult blood, and to observe the composition for the characteristic color change. The diagnostic aid and method for determining the presence of occult blood in accordance with the present invention do not require the handling of feces samples or the application of the same to a paper substrate. Neither does the present invention require the handling or application of a liquid developing solution to a substrate or carrier. Instead, in accordance with the present invention, a single, dry package containing all of the required test reactants is placed in contact with the aqueous medium and thereafter observed for the blue dye that results from the guaiac oxidation reaction. Additionally, a positive reaction with the diagnostic aid prepared in accordance with the present invention yields a bright, vivid blue dye that is very easy to interpret, even by the inexperienced home user.

Although the present invention has been described in terms of a preferred embodiment and various alternatives thereto, one of ordinary skill after reading the foregoing specification will be able to effect various changes, substitutions of equivalents, and other alterations without departing from the broad concepts disclosed herein. For example, a small amount of hemoglobin can be incorporated into the diagnostic aid as a comparison control to assist the ordinary person in correctly interpreting a positive test result. The hemoglobin can be impregnated into a designated location on the filter paper in which reactant compositions are packaged. The user of the aid, of course, would be instructed of the location of the control so that the blue dye produced by the presence of hemoglobin at the designated location would not be mistaken for a positive test, but rather would be used only as an interpretation aid. It is therefore intended that the scope of protection granted by Letters Patent hereon be limited only by the definition contained in the appended claims and equivalents thereof.

The embodiments of the invention in which an exclusive property or privilege is claimed are defined as follows:

1. An essentially dry, one-step diagnostic aid for determining the presence of hemoglobin in fecal matter in an aqueous environment comprising:
    a dry adsorbent carrier having guaiac adsorbed thereon said carrier selected from the group consisting of adsorbed silica-based materials, calcium phosphate, and mixtures thereof, the carrier holding said guaiac readily available to react in the presence of hemoglobin and an oxidizing agent in an aqueous environment to yield to blue dye; and
    a dry oxidizing agent consisting essentially of a monopersulfate compound capable of oxidizing said guaiac to a blue dye in the presence of water and hemoglobin, said oxidizing agent in the absence of water being substantially nonreactive with said guaiac adsorbed onto said carrier; and
    a binder into which the carrier and oxidizing agent have been compressed to form a tablet.

2. The aid of claim 1, wherein said carrier is silica gel.

3. The aid of claim 1, wherein said oxidizing agent and said carrier containing said guaiac are present in a weight ratio of from about 1:3 to about 3:1.

4. The aid of claim 3 wherein the weight ratio of the oxidizing agent to the carrier is 1 to 1.

5. The aid of claim 1, wherein said oxidizing agent is a triple salt of potassium monopersulfate, potassium hydrogen sulfate, and potassium sulfate.

6. The aid of claim 1, wherein the diagnostic aid further comprises an effervescent material which produces a gas upon contact with an aqueous medium.

7. A method for producing an essentially dry, one-step diagnostic aid for determining the presence of hemoglobin in fecal matter in an aqueous environment comprising:
    selecting a dry adsorbent particulate carrier from the group consisting of adsorbent silica-based materials, calcium phosphate, and mixtures thereof;
    placing a solution of guaiac in a solvent in contact with the particulate carrier;
    drying the particulate carrier to evaporate the solvent, leaving the particulate carrier with the guaiac substantially dried thereon;
    selecting a dry oxidizing agent consisting essentially of a monopersulfate compound;
    selecting a suitable binder; and
    compressing the guaiac-adsorbed carrier, oxidizing agent, and binder to form a tablet.

8. The method of claim 7, wherein said solvent is selected from the group consisting of a lower aliphatic alcohol, chloroform, benzene and mixtures thereof.

9. The method of claim 7, wherein said solvent is selected from the group consisting of an alkenol having from one to six carbon atoms, an alkanol having from one to six carbon atoms, chloroform, benzene and mixtures thereof.

10. The method of claim 7, wherein said solvent is selected from the group consisting of methanol, isopropanol, chloroform, benzene and mixtures thereof.

11. The method of claim 7, wherein the particulate carrier is silica gel and a ratio of the guaiac solution contacting the silica gel is in a range of 1 ml solution to 6 g silica gel to 15 ml solution to 1 g silica gel.

12. The method of claim 11 wherein the ratio is 1 ml guaiac solution to 1 g silica gel.

13. A method for determining the presence of hemoglobin in an aqueous medium containing fecal material, comprising:
    providing a tablet comprised of a dry adsorbent particulate carrier selected from the group consisting of adsorbent silica-based materials, calcium phosphate, and mixtures thereof having guaiac adsorbed thereon, a dry oxidizing agent essentially of a monopersulfate compound, and a suitable binder, the oxidizing agent reacting with the guaiac in the presence of hemoglobin in an aqueous medium to yield a blue dye, the oxidizing agent in the absence of water being substantially nonreactive with said guaiac;
    placing the tablet into an aqueous medium containing fecal matter; and
    observing whether a blue dye is formed, thereby indicating the presence of hemoglobin.

* * * * *